United States Patent [19]

Durance et al.

[11] Patent Number: 4,966,851

[45] Date of Patent: Oct. 30, 1990

[54] PROCESS FOR ISOLATION OF LYSOZYME AND AVIDIN FROM EGG WHITE

[75] Inventors: Timothy Durance; Eunice Li-Chan; Shuryo Nakai, all of Vancouver, Canada

[73] Assignee: The University of British Columbia, Vancouver, Canada

[21] Appl. No.: 122,848

[22] Filed: Nov. 19, 1987

[30] Foreign Application Priority Data

Dec. 1, 1986 [CA] Canada .................................. 524200

[51] Int. Cl.$^5$ ......................... C12N 9/36; C07K 3/18; C07K 3/22
[52] U.S. Cl. .................... 435/206; 435/803; 435/815; 530/368; 530/416
[58] Field of Search ....................... 435/206, 803, 815; 530/368, 416, 853

[56] References Cited

U.S. PATENT DOCUMENTS 3,515,643 6/1970 Ghielmetti et al. ................. 435/206

FOREIGN PATENT DOCUMENTS

| | | |
|---|---|---|
| 763403 | 7/1967 | Canada . |
| 812767 | 5/1969 | Canada . |
| 829279 | 12/1969 | Canada . |
| 832997 | 1/1970 | Canada . |
| 884288 | 10/1971 | Canada . |
| 62-000500 | 1/1987 | Japan .................. 435/206 |
| 63-222200 | 9/1988 | Japan .................. 530/368 |

OTHER PUBLICATIONS

Green, "Purification of Avidin," in Methods in Enzymology, vol. XVIII, Part A, McCormick et al., Ed., pp. 414–417, 1970.

Li-Chan et al., *J. of Food Sci.*, vol. 51, No. 4, (1986), pp. 1032–1036.

*Primary Examiner*—David M. Naff
*Attorney, Agent, or Firm*—Bernard, Rothwell & Brown

[57] ABSTRACT

A process for the isolation and separation of lysozyme and avidin from egg white is carried out by:

step (a) contacting egg white with a weakly acidic cation exchange resin whereby lysozyme and avidin are adsorbed on to the resin; separating the resin from the egg white and washing the resin to remove residual egg white therefrom; and contacting the washed resin with a low ionic strength eluting buffer whereby lysozyme is eluted from the resin while avidin remains adsorbed on the resin; and step (b) repeating the complete procedure defined in step (a) for two or more times; and step (c) finally contacting the resin containing accumulated adsorbed avidin with a high ionic strength eluting buffer whereby avidin is eluted from the resin.

Lysozyme and avidin are both commercial products useful, for example, in pharmaceutical applications.

9 Claims, No Drawings

PROCESS FOR ISOLATION OF LYSOZYME AND AVIDIN FROM EGG WHITE

This invention relates to a novel process for the isolation and separation of lysozyme and avidin from hen egg white (hereinafter referred to simply as egg white). More particularly, this invention relates to a novel process for the isolation of avidin in good yield and in good quality from egg white.

It is known (Li-Chan et al. Journal of Food Science 1986, Vol. 51, No. 4, pages 1032–1036) that lysozyme may be isolated from egg white by means of a cation exchange column chromatographic procedure using the resin known as *Duolite C-464 followed by elution. This process produces lysozyme in admixture with small quantities of avidin under the elution conditions described.

* Trade Mark

We have now found, and herein lies our invention, that lysozyme and avidin can be isolated as the two desired products from egg white by use of a particular cation exchange resin in combination with two different eluting buffers.

Thus, according to the invention as claimed herein, we provide a process for the isolation and separation of lysozyme and avidin from egg white which comprises:

step (a) contacting egg white with a weakly acidic cation exchange resin whereby lysozyme and avidin are adsorbed on to said resin; separating said resin from said egg white and washing said resin to remove residual egg white therefrom; and contacting said washed resin with a low ionic strength eluting buffer whereby lysozyme is eluted from said resin while avidin remains adsorbed on said resin; and step (b) repeating the complete procedure defined in step (a) for two or more times; and step (c) finally contacting said resin containing accumulated adsorbed avidin with a high ionic strength eluting buffer whereby avidin is eluted from said resin.

The invention as described and claimed herein is a process for the isolation and separation of lysozyme and avidin from egg white on a weakly acidic cation exchange resin with two different eluting buffers and such a process does not adversely affect the functional or nutritional properties of the remaining egg white after such a procedure.

Lysozyme and avidin are proteins found in low concentrations in egg white. Both are of considerable commercial value and, furthermore, their removal from egg white does not significantly decrease the economic value of the remaining egg white. The novel process described and claimed herein for the isolation and separation of these two proteins by use of a weakly acidic cation exchange resin in combination with a unique varying buffer system from a low to a high ionic strength eluting buffer, causes lysozyme to elute before avidin. This result is unexpected since such a stepwise elution is the reverse of the usual elution order for these proteins. Avidin is much less abundant than lysozyme in egg white (1:70) and because both products have similar charge properties, the recovery of avidin which is not heavily contaminated with lysozyme is difficult to achieve by use of the usual, known chromatographic processes. However, in the novel process described and claimed herein, it is possible to perform several cycles of egg white application to a weakly acidic cation exchange resin followed by elution of lysozyme, while allowing the avidin to accumulate on the resin. This procedure increases the purity and concentration of the avidin fraction when it is finally eluted from the resin and, at the same time, lysozyme is obtained in excellent yield and purity.

It is to be understood that the weakly acidic cation exchange resin to be used in the present process is one such that both lysozyme and avidin are adsorbed by the resin but other egg white proteins are not so adsorbed and, in addition, avidin is adsorbed more strongly than lysozyme. A variety of different resins may be used for this process and such weakly acidic cation exchange resins include *Duolite C-464, carboxymethyl-*Sepharose, *Biorex 70, *Amberlite IRC-50, CG-50, DP-1, IRC-72 and IRP-64, *Rexyn 102, *Merck IV, *Zeocarb 226, *Diaion WK10 and WK11, *Imac Z-5, *CP-3050 and *Wofatit CP300. Of these resins, the resin of choice is *Duolite C-464 which is a macroporous cross-linked polyacrylic acid with carboxylic exchange groups. This type of resin consists of copolymers formed from the copolymerization of methacrylic acid and p-divinylbenzene. Another useful resin is carboxymethyl-*Sepharose which is a carboxymethyl agarose gel having carboxylic acid exchange groups.

* Trade Mark

It is to be understood that a suitable low ionic strength eluting buffer is one which will elute lysozyme from the weakly acidic cation exchange resin but will not elute avidin. It is generally found that a preferred low ionic strength eluting buffer may be a phosphate buffer containing a relatively small proportion of sodium chloride since such eluting buffers are non-toxic and economical in use. As examples of these low ionic strength eluting buffers there may be mentioned (a) 0.1M sodium phosphate+0.12M sodium chloride, (b) 0.1M sodium phosphate+0.13M sodium chloride, (c) 0.1M sodium phosphate+0.15M sodium chloride, and (d) 0.05M sodium phosphate+0.20M sodium chloride. Other combinations of these buffer concentrations (sodium phosphate) and salt concentrations (sodium chloride) may be used or alternative buffers and salts may be used to provide low ionic strength eluting buffers. Examples of buffers are 0.05 to 0.1M sodium phosphate, ammonium carbonate or sodium carbonate or a mixture of 0.05M ammonium acetate and 0.05M ammonium carbonate while examples of salts are sodium chloride, ammonium chloride or ammonium sulphate, the concentrations of the buffer and the salt used being such as to provide a low ionic strength eluting buffer, as defined above.

It is likewise to be understood that a suitable high ionic strength eluting buffer is a buffer which will elute avidin from the resin. It has been found that a preferred high ionic strength eluting buffer is one which contains sodium phosphate as the buffer with a relatively large proportion of sodium chloride as the salt. Such high ionic strength eluting buffers may be (a) 0.1M sodium phosphate +0.4M sodium chloride, (b) 0.1M sodium phosphate +0.6M sodium chloride, or (c) 0.1M sodium phosphate +1.0M sodium chloride. Other suitable combinations of a buffer and a salt may be prepared from the buffers and salts mentioned hereinbefore provided that the high ionic strength eluting buffer thus prepared is useful to elute avidin from the resin.

The process may be carried out at a pH which is suitable for the particular resin and the buffer system which is used. We have found that a particularly preferred pH is from about 7.5 to about 8.3 for the process.

The pH must be below 9.8 which is the maximum pH at which avidin binds to a weakly acidic cation exchange resin. An acidic pH is to be avoided since it tends to cause denaturation and precipitation of certain egg white proteins. Thus, the broadest range of suitable pH for carrying out the process of the invention is from about pH 6.5 to about pH 9.5.

In its simplest form, the process of our invention may be carried out as a batch process in a vat or a similar container. For example, the weakly acidic cation exchange resin such as *Duolite C-464 may be prepared and equilibrated with 0.1M sodium phosphate buffer at pH 7.9. The equilibrated resin thus prepared may be added to, and stirred with, egg white contained in a vat or large container. The resin is then removed from the egg white and the resin is washed with water or with a buffer to remove residual egg white without removing lysozyme or avidin. Water is preferred but an equilibration buffer (0.05-0.1M sodium phosphate at pH 7.5 to 8.0) may be used. After the washing procedure, the lysozyme can be removed from the resin by mixing the resin with a low ionic strength eluting buffer. After such treatment, the resin may be placed in contact with a second quantity of egg white. The washing, removal of lysozyme and further contact with egg white may be repeated up to 10 or 20 times until sufficient avidin has accumulated on the resin. Finally, the accumulated avidin may be eluted from the resin by immersion of the resin in a high ionic strength eluting buffer.
* Trade Mark In an alternative procedure, the weakly acidic cation exchange resin may be placed in a column for a chromatographic procedure such that the process of this invention may be carried out as a continuous operation.

Thus, according to a further feature of the invention as claimed herein we provide a process for the isolation and separation of lysozyme and avidin from egg white which comprises:
step (a) passing egg white through a column containing a weakly acidic cation exchange resin whereby lysozyme and avidin are adsorbed on to said resin; washing said resin to remove residual egg white therefrom; and eluting lysozyme from said resin by use of a low ionic strength eluting buffer whereby avidin remains adsorbed on said resin; and
step (b) repeating the complete procedure defined in step (a) above two or more times; and
step (c) finally eluting avidin from said resin by use of a high ionic strength eluting buffer.

A suitable chromatographic column can be prepared using *Duolite C-464 cation exchange resin. The packed column is equilibrated by the passage of a 0.1M sodium phosphate buffer at pH 7.9 through the resin.
* Trade Mark Egg white from hens eggs which has been separated from the yolk and shell components is given a pretreatment by passing it through a conventional single stage milk homogenizer (homogenization pressure=6.9 MPa) in order to reduce the viscosity of the egg white.

The pretreated egg white may then be pumped on to the column containing *Duolite C-464 resin such as to allow a contact time between the egg white and the resin of about 30 minutes. It is preferable that the flow of egg white, and subsequent flow of other liquids through the resin, be made in an upward flow direction in order to avoid changes in volume of the resin with undesirable compacting or severe packing of the resin bed leading to difficulty in controlling flow rates. The resin is an efficient adsorber of lysozyme and avidin and it is possible to pass a substantial volume of egg white through the resin and maintain efficient adsorption. The optimum ratio of the volume of egg white to the volume of resin used in the column will vary according to each particular resin, but in the case of *Duolite C-464, it has been found that 3 to 4 volumes of egg white can be applied per 1 volume of resin with successful adsorption.
* Trade Mark When the egg white has passed through the resin, it is necessary to wash the resin with water or an appropriate aqueous buffer in order to remove residual egg white and traces of unadsorbed matter from the resin. When using water as the washing medium, a volume of water approximately equal to the volume of the egg white is a suitable amount of wash water and it may be passed through the resin at a flow rate which is about twice the flow rate of the egg white application. When using an aqueous buffer as the washing medium, the buffer should be one which does not cause elution of lysozyme or avidin from the resin. Thus., the ionic strength and the pH of the buffer should be low enough to avoid elution of lysozyme. An equilibration buffer, for example 0.05 to 0.1M sodium phosphate at pH 7.5 to 8.0, is suitable. Water is preferred as a washing medium because of ease of supply and economic factors.

Following the washing of the resin, lysozyme may be eluted from the resin by use of a low ionic strength eluting buffer solution, while avidin remains adsorbed on the resin. As a suitable eluting buffer there may be mentioned, an aqueous solution containing an alkali metal phosphate, such as sodium phosphate, and an alkali metal chloride, such as sodium chloride at a pH of from about 7.5 to about 8.3. A preferred eluting solution is 0.1M sodium phosphate containing 0.15M sodium chloride having a pH of about 7.9. Other low ionic strength eluting buffers suitable for eluting lysozyme have been described hereinbefore. The eluting buffer may be passed through the resin at a flow rate approximately equal to that of the egg white. The volume of this eluting buffer may be equal to, or up to twice, the volume of egg white applied to the resin. The eluting procedure removes substantially all of the lysozyme from the resin and the eluate contains essentially lysozyme while the avidin remains adsorbed on the resin.

The procedure of applying egg white to the resin, washing the resin and then eluting the resin to remove lysozyme, as described above in step (a), is repeated several times in order to allow avidin to accumulate on the resin according to step (b). The procedure of step (a) may be repeated four or more times, preferably 10 or 20 or more times depending upon the volume of egg white treated in each cycle, the volume of resin used and the amount of lysozyme and avidin in the original egg white. We have found that repeating the procedure of step (a) for about 10 or 20 or more times results in a satisfactory accumulation of avidin on the resin and the avidin subsequently eluted therefrom is of high purity and in high yield.

When the procedure of step (a) has been repeated for a satisfactory number of cycles and thus step (b) has been completed to accumulate sufficient avidin on the resin, the avidin may then be eluted from the resin according to step (c) by use of a high ionic strength eluting buffer. As a suitable buffer, there may be mentioned, for example, a buffer containing an alkali metal phosphate, such as sodium phosphate, together with an alkali metal chloride, such as sodium chloride, in sufficient concentration to provide the high ionic strength. The pH of such a buffer is preferably from about 7.5 to about 8.3. A suitable eluting buffer to be used is an aqueous solution containing about 0.1M sodium phosphate and from about 0.4M to about 1.0M sodium chloride at a pH of about 7.9. A preferred eluting buffer is 0.1M sodium phosphate and 1.0M sodium chloride at pH of about 7.9. The flow rate of the high ionic strength eluting buffer is preferably about one half the flow rate of the egg white application. When the avidin has been eluted from the resin, the eluate containing the avidin may be a volume approximately equal to the volume of egg white applied in a single passage as defined in step (a).

The avidin solution obtained as eluate may be used without further purification for certain purposes. If a more highly purified form of avidin is desired, the avidin may be further purified by a chromatographic procedure using carboxymethylcellulose followed by elution, according to established methods known to the art. It may also be further purified by immobilized metal affinity chromatography or by gel filtration. If necessary, the avidin obtained according to this process may be further processed, if desired, in order to remove excess salts and water. This may be achieved, for example, by dialysis or by ultrafiltration.

The invention is illustrated but not limited by the following Examples:

EXAMPLE 1

(a) A column (5.0 cm×24.0 cm) of *Duolite C-464 cation exchange resin was prepared and equilibrated with 0.1M sodium phosphate buffer at pH 7.9.
* Trade Mark (b) Two liters of homogenized egg white was passed through the resin, in an upward direction, at a flow rate of 8 ml/min., and the egg white leaving the top of the column was collected and labelled "egg white minus lysozyme and avidin".

(c) Following the egg white, two liters of distilled water was passed upward through the resin at a flow rate of 16 ml/min., and the water leaving the column was discarded.

(d) Following the water, two liters of "low ionic strength eluting buffer" (0.1M sodium phosphate with 0.15M sodium chloride, at pH 7.9) was passed upward through the resin at a flow rate of 8 ml/min. and was collected, and labelled "cycle 1. lysozyme". More than 80% of the lysozyme from the egg white was recovered. The lysozyme fraction appeared pure when examined by sodium dodecyl sulphate-polyacrylamide gel electrophoresis.

(e) Next, steps (b), (c) and (d) were repeated exactly as above for four more times.

(f) Finally, after the five cycles of (b), (c) and (d) have thus been completed, two liters of "high ionic strength" buffer (0.1M sodium phosphate with 1.0M sodium chloride, at pH 7.9) was passed upward through the resin to elute the adsorbed avidin and labelled "avidin fraction". Eighty percent of the avidin in the egg white was recovered. The purity of the avidin fraction was 12% (i.e. mg avidin/mg protein×100%).

EXAMPLE 2

The process of Example 1 was repeated except that 10 cycles, instead of 5 cycles, of the steps (b), (c) and (d) were passed through the resin before the avidin was eluted in step (f). Approximately 80% of the avidin was recovered but the purity of the avidin fraction was increased to 25%.

EXAMPLE 3

The process of Example 1 was repeated except that 20 cycles, instead of 5 cycles, of the steps (b), (c) and (d) were passed through the resin before the avidin was eluted in step (f). Approximately 80% of the avidin was recovered but the purity of the avidin fraction was increased to 50%.

For comparison, when only a single cycle of steps (b), (c) and (d) was passed through the resin before avidin was eluted, approximately 80% of the avidin was recovered, but the purity of the avidin fraction was only 4%.

The embodiments of the invention in which an exclusive property or privilege is claimed are defined as follows:

1. A process for the isolation and separation of lysozyme and avidin from egg while which comprises:
    step (a) contacting egg white with a weakly acidic cation exchange resin having a greater affinity for avidin than for lysozyme, whereby lysozyme and avidin are adsorbed on to said resin;
    separating said resin from said egg white and washing said resin to remove residual egg white therefrom; and
    contacting said washed resin with a low ionic strength eluting buffer whereby lysozyme is eluted from said resin while avidin remains adsorbed on said resin; and
    step (b) repeating the complete procedure defined in step (a) for two or more times; and
    step (c) finally contacting said resin containing accumulated adsorbed avidin with a high ionic strength eluting buffer whereby avidin is eluted from said resin.

2. A process for the isolation and separation of lysozyme and avidin from egg white which comprises:
    step (a) passing egg white through a column containing a weakly acidic cation exchange resin having a greater affinity for avidin than for lysozyme, whereby lysozyme and avidin are adsorbed on to said resin;
    washing said resin to remove residual egg white therefrom; and eluting lysozyme from said resin by use of a low ionic strength eluting buffer whereby avidin remains adsorbed on said resin; and
    step (b) repeating the complete procedure defined in step (a) above two or more times; and
    step (c) finally eluting avidin from said resin by use of a high ionic strength eluting buffer.

3. The process of claim 2 wherein the resin is a polymer which is a cross-linked polyacrylic acid derivative.

4. The process of claim 2 wherein the resin is a copolymer formed from methacrylic acid and 1,4-divinylbenzene.

5. The process of claim 2 wherein the resin is an agarose gel having carboxylic acid groups.

6. The process of claim 2 wherein the process is carried out within a pH range of from about 7.5 to about 8.3.

7. A process for the isolation and separation of lysozyme and avidin from egg white which comprises:
    step (a) passing egg white in an upward flow direction through a column containing a weakly acidic cation exchange resin having a greater affinity for avidin than for lysozyme, whereby lysozyme and avidin are adsorbed on to said resin;

washing said resin with water to remove residual egg white therefrom; and eluting lysozyme from said resin by use of a low ionic strength eluting buffer whereby avidin remains adsorbed on said resin; and step (b) repeating the complete procedure defined in step (a) above at least about ten more times; and step (c) finally eluting avidin from said resin by use of a high ionic strength eluting buffer.

8. The process of claim 7 wherein the ratio of the volume of egg white to the volume of the cation exchange resin is from about 3:1 to about 4:1.

9. A process for the isolation and separation of lysozyme and avidin from egg white which comprises:

step (a) passing a volume of egg white in an upward flow direction through a column containing a weakly acidic cation exchange resin having a greater affinity for avidin than for lysozyme, whereby lysozyme and avidin are adsorbed on to said resin, the ratio of the volume of said egg white to the volume of said resin being about 4:1 and the contact time between the egg white and the resin being about 30 minutes;

washing said resin with water, the ratio of the volume of water to the volume of egg white passage being about 1:1 and the ratio of the flow rate of the water to the flow rate of the egg white passage being about 2:1; and eluting lysozyme from the resin by use of an aqueous buffer containing 0.1M sodium phosphate and 0.15M sodium chloride at a pH of about 7.9, the ratio of the volume of the buffer to the volume of the egg white being about 2:1 and the ratio of the flow rate of the buffer to the flow rate of the egg white being about 1:1; and step (b) repeating the complete procedure defined in step (a) above at least about ten more times; and step (c) finally eluting avidin from the resin by use of an aqueous buffer containing 0.1M sodium phosphate and 1.0M sodium chloride at a pH of about 7.9, the ratio of the volume of buffer to the volume of a single egg white passage being about 1:1 and the ratio of the flow rate of buffer to the flow rate of egg white passage being about 0.5:1.

* * * * *